United States Patent [19]

Kitazume

[11] Patent Number: 5,097,075

[45] Date of Patent: Mar. 17, 1992

[54] 1,1,1-TRIFLUORO-2-HYDROXY COMPOUND

[75] Inventor: Tomoya Kitazume, Tokyo, Japan

[73] Assignee: Showa Shell Sekiyu Kabushiki Kaisha, Tokyo, Japan

[21] Appl. No.: 595,821

[22] Filed: Oct. 10, 1990

[30] Foreign Application Priority Data

Oct. 16, 1989 [JP] Japan .................................. 1-266318
Oct. 16, 1989 [JP] Japan .................................. 1-266319
Oct. 30, 1989 [JP] Japan .................................. 1-279996

[51] Int. Cl.$^5$ .................. C07C 43/164; C07C 43/166
[52] U.S. Cl. ................................. 568/583; 435/135; 435/157; 549/551
[58] Field of Search ........................................ 568/583

[56] References Cited

U.S. PATENT DOCUMENTS 3,627,847 12/1971 Langkammerer .................. 568/583
4,182,911 1/1980 Tucker ................................ 568/583

OTHER PUBLICATIONS

Patent Abstracts of Japan, vol. 13, No. 388 (C-630)[3736], 28 Aug. 1989; & JP-A-1 137 996 (Showa Shell Sekiya K.K.) 30-05-1989; JP-A-137 781 (Showa Shell Sekiyu K.K.) 29-05-1989; JP-A-1 135 738 (Showa Shell Sekiyu K.K.) 29-05-1989.

*Primary Examiner*—J. E. Evans
*Attorney, Agent, or Firm*—Cushman, Darby & Cushman

[57] ABSTRACT 1,1,1-Trifluoro-2-hydroxy-5-benzyloxy compounds represented by the following formula (I) and optical isomers thereof:

CF$_3$CH(OH)—X—CH$_2$OCH$_2$—C$_6$H$_5$  (I)

wherein X is —C≡C—, —CH=CH—, —CH—CH— (epoxide) or

—CH(NH-C$_6$H$_5$)—CH(OH)— group.

The compounds of the present invention are R-form and S-form when X is —C≡C— and are trans-form and cis-form both of which have respectively R-form and S-form when X is —CH=CH— or —CH—CH— (epoxide).

the compound of the present invention is

CF$_3$CH(OH)—CH(NH-C$_6$H$_5$)—CH(OH)—CH$_2$OCH$_2$—C$_6$H$_5$

The compounds of the present invention are useful for asymmetric introduction of trifluoromethyl group and molecular designing of biologically active substances, ferroelectric liquid crystal compounds and so on.

2 Claims, No Drawings

1,1,1-TRIFLUORO-2-HYDROXY COMPOUND

The present invention relates to optically active 1,1,1-trifluoro-2-hydroxy-5-benzyloxy compounds and a process for asymmetrically introducing the trifluoromethyl group by incorporating the hydroxy group at the 2-position to the other molecules. The compounds have industrial significance in molecular designing of biologically active substances, ferroelectric liquid crystal compounds and so on.

Fluorine compounds have specificity as compared with hydrocarbons. It is considered that this specificity is based on higher electronegativity of the fluorine atom than the other atoms, sterically small molecular volume next to the hydrogen, and large carbon-fluorine bond energy.

Fluorine atom has the highest electronegativity among all elements (F: 4.00, O: 3.50, Cl: 3.15, N: 3.05). This means that electron density of carbons at α-position and β-position of the C-F bond is made smaller. For instance, when it has an amino group at the α-position, basicity of the amino group is made extremely small and, when it has an hydroxyl group at the β-position, the behavior of the hydroxyl group is more acidic. In some cases, the fluorine atom influences conformation of the whole molecule. Therefore, when a compound is modified with a fluorine atom, especially a trifluoromethyl group, chemical properties and reactivity of the compound per se undergo conspicuous change and in some cases, organic synthesis methods are hardly used freely.

Hitherto, introduction of a fluorine atom or a fluorine-containing group into a compound has been mostly conducted by direct fluorination method by using fluorinating agents. For example, fluorination of alcohols is conducted with organic reagents such as HPDA reagent (hexafluoropropenedialkylamine adduct) and DAST reagent (dialkylaminosulfur trifluoride). Furthermore, halogen exchanging process by metal fluorides such as CsF, KF, and AgF or TBAF (tetrabutylammonium fluoride) has been well known to be used for tosylate, mesylate and halides derived from alcohols. In additinn, there are fluorination by ring opening of oxirane, addition reaction of fluorine to double bonds, and fluorination of carbonyl compounds.

As explained above, synthesis of various optically active trifluoromethyl-containing compounds has become relatively simple, but for molecular designing of biologically active substances based on these optically active substances, asymmetric propagation to a plurality of carbon atoms in the molecule becomes necessary. In such case, asymmetric induction to carbon in the molecule of optically active compounds having a trifluoromethyl group is difficult and has limit due to specificity of fluorine atoms when modified with fluorine atoms, especially a trifluoromethyl group.

The present invention provides compounds represented by the formula (I) and optical isomers thereof, and a process for preparation thereof.

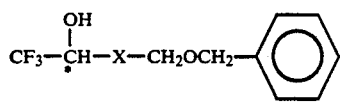

(I)

-continued

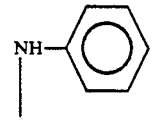

wherein X is $-C\equiv C-$, $-CH=CH-$ or $-CH-CH(OH)-$

The present invention has established a process for obtaining optically active 1,1,1-trifluoro-2-hydroxy-5-benzyloxy-3-pentyne, wherein propargyl alcohol which is inexpensive and readily available, is used as a starting material, 1,1,1-trifluoro-2-hydroxy-5-benzyloxy-3-pentyne is once prepared, and the pentyne compound is subjected to optical resolution by use of enzyme or lipase until optically active 1,1,1-trifluoro-2-hydroxy-5-benzyloxy-3-pentyne, optically active 1,1,1-trifluoro-2-hydroxy-5-benzyloxy-3-pentene and 1,1,1-trifluoro-3-(N-phenylamino-5-benzyloxypentane-2,4-diol are obtained.

Route of chemical reaction according to the present invention will be explained below.

(1) Propargyl alcohol is allowed to react with chloromethylbenzyl ether to obtain 1-benzyloxy-2-propyne (1). Then, this is allowed to react with Grignard reagent and a trifluoroacetic acid ester to obtain 5-benzyloxy-1,1,1-trifluoro-3-pentyne-2-one (2). Then, this is allowed to react with hydride of boron or aluminum to obtain 5-benzyloxy-1,1,1-trifluoro-3-pentyne-2-ol (3). This is acetylated or isobutylated and thereafter lipase or lipase-producing microorganism is allowed to act thereon to obtain optically active (R)-5-benzyloxy-1,1,1-trifluoro-3-pentyne-2-ol [(R)-(3)] and optically active (S)-5-benzyloxy-1,1,1-trifluoro-2-acetoxy (or butoxy)-3-pentyne [(S)-(4)].

Furthermore, if necessary, (S)-5-benzyloxy-1,1,1-trifluoro-2-hydroxy-3-pentyl [(S)-(4)] is also obtained by hydrolysis of acetate (or isobutoxylate) of the above (S)-(4).

The above process is shown by reaction formula as follows.

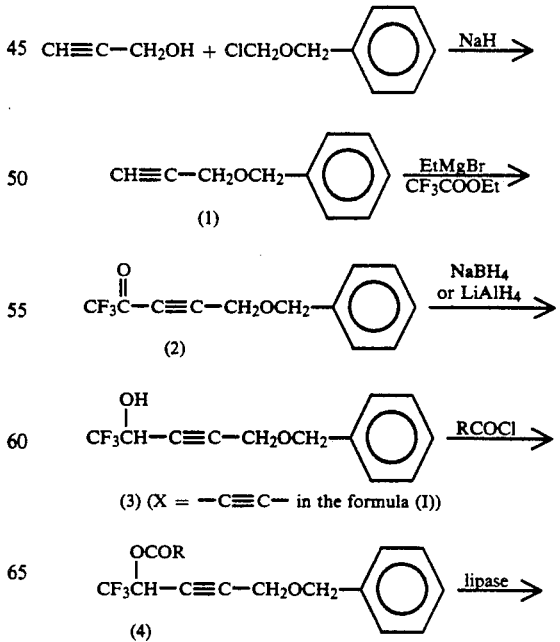

1,1,1-trifluoro-3-pentene-2-ol (E)-(5) or (Z)-(5). This is acetylated or isobutylated and then thereon is allowed lipases or lipases-producing microorganism to act to obtain optically active (R)-5-benzyloxy-1,1,1-trifluoro-3-pentene-2-ol [(R)-(E)-5] or [(R)-(Z)-5] and optically active (S)-2-acetoxy (or butoxy)-5-benzyloxy-1,1,1-trifluoro-3-pentene [(S)-(E)-6 or (S)-(Z)-6].

Furthermore, if necessary, 5-benzyl-oxy-1,1,1-trifluoro-3-pentene-2-ol [(S)-(E)-(5) or (S)-(Z)-(5)] can also be obtained by hydrolysis of acetate or isobutoxylate of the above [(S)-(E)-6[ or ](S)-(Z)-6].

The above reaction is shown by chemical formula as follows:

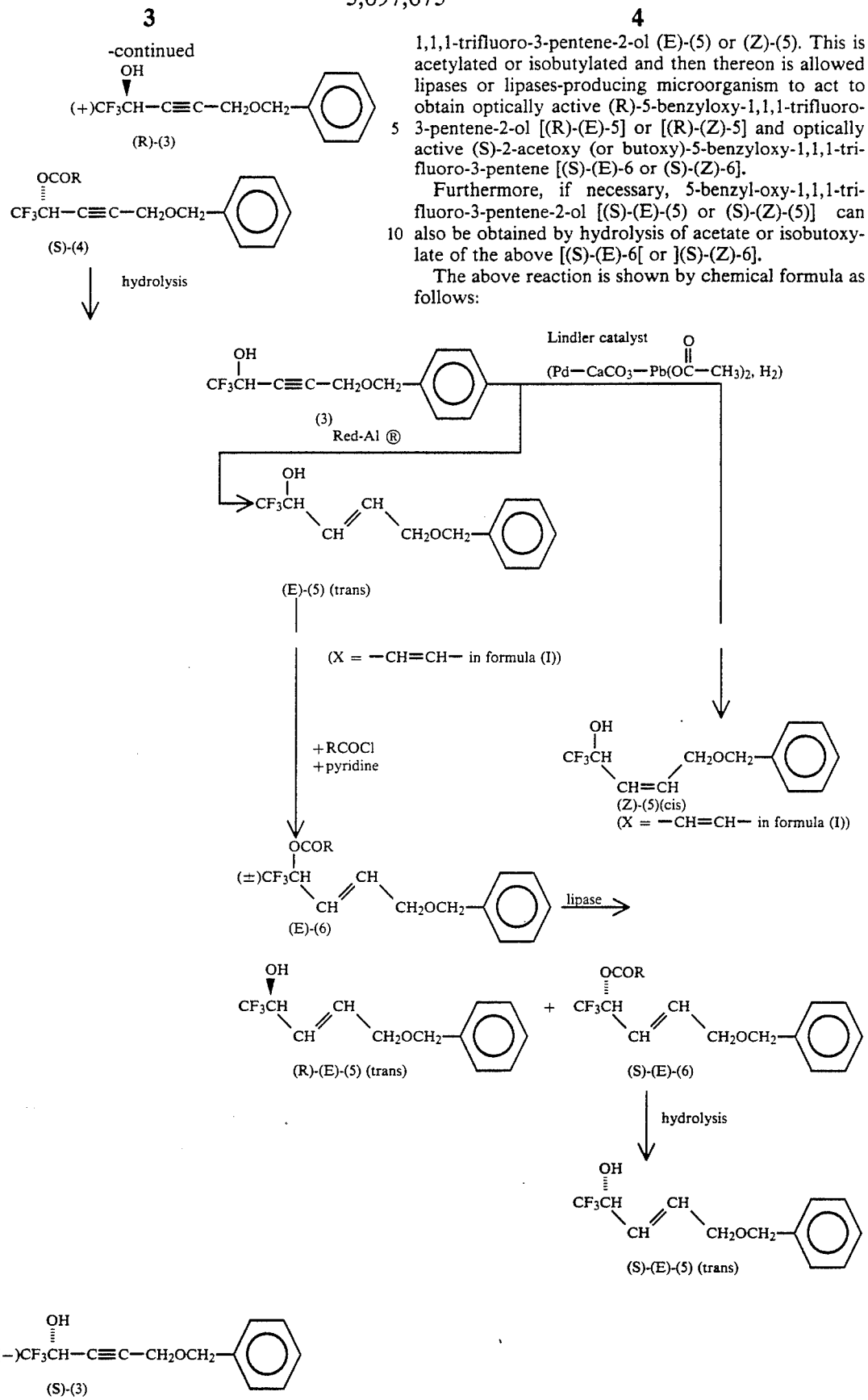

Next, a hydride of boron or aluminum or palladium catalyst is allowed to act on 5-benzyloxy-1,1,1-trifluoro-3-pentyne-2-ol (compound (3)) to obtain 5-benzyloxy- The following optical isomers are obtained also for (Z)-(5) by asymmetric resolution in the same manner as for (E)-(5).

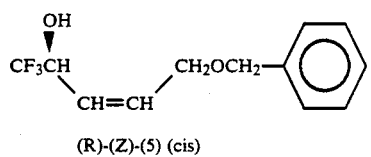

(R)-(Z)-(5) (cis)

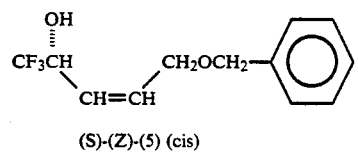

(S)-(Z)-(5) (cis)

Alternatively, the following reaction may be obtained.

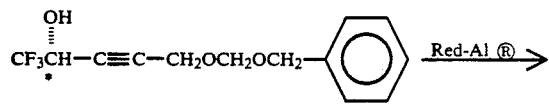

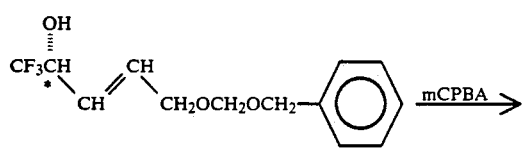

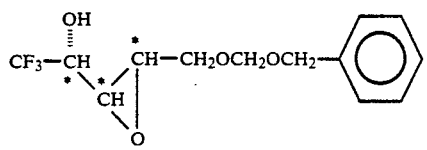

Optically active compounds produced by the present process are as follows:

| Configuration | Chemical structure |
|---|---|
| (S)-(E) | ![structure] OH, CF₃, O, O, Ph |
| (S)-(Z) | ![structure] OH, CF₃, O, O, Ph |
| (R)-(E) | ![structure] OH, CF₃, O, O, Ph |
| (R)-(Z) | ![structure] OH, CF₃, O, O, Ph |
| (S)-(E) | ![structure] OH, CF₃, O, Ph |
| (S)-(Z) | ![structure] OH, CF₃, O, Ph |
| (R)-(E) | ![structure] OH, CF₃, O, Ph |
| (R)-(Z) | ![structure] OH, CF₃, O, Ph |

Furthermore, 5-benzyloxy-1,1,1-trifluoro-3-pentene-2-ol [(E)-(5) or (Z)-(5)] is allowed to react with a peroxide of an organic acid to obtain 5-benzyloxy-trans or cis-3,4-epoxy-1,1,1-trifluoro-2-pentanol (7).

Then, the above epoxide (7) is allowed to react with an isocyanic acid ester to obtain 5-benzyloxy-trans (or cis)-3,4-epoxy-2-[(N-phenylcarbamoyl)oxy]-1,1,1-trifluoropentane (8). Then, the resulting compound (8) is allowed to react with an alkali metal alcoholate to obtain a mixture of the above trans epoxide (7) or cis epoxide (7') and urethan (9). This mixture is allowed to react with an alkali metal hydroxide to obtain the above trans epoxide (7) or cis epoxide (7') and 5-benzyloxy-3-(N-phenylamino)-1,1,1-trifluoropentane-2,4-diol (10).

The above compounds (7) and (10) are both optically active compounds having three continuous asymmetric points.

The above reaction is shown by chemical formula as follows:

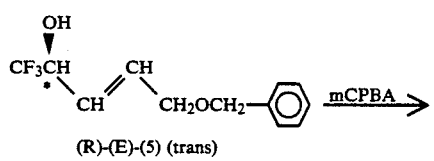

(R)-(E)-(5) (trans)

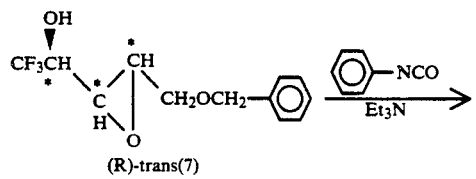

(R)-trans(7)

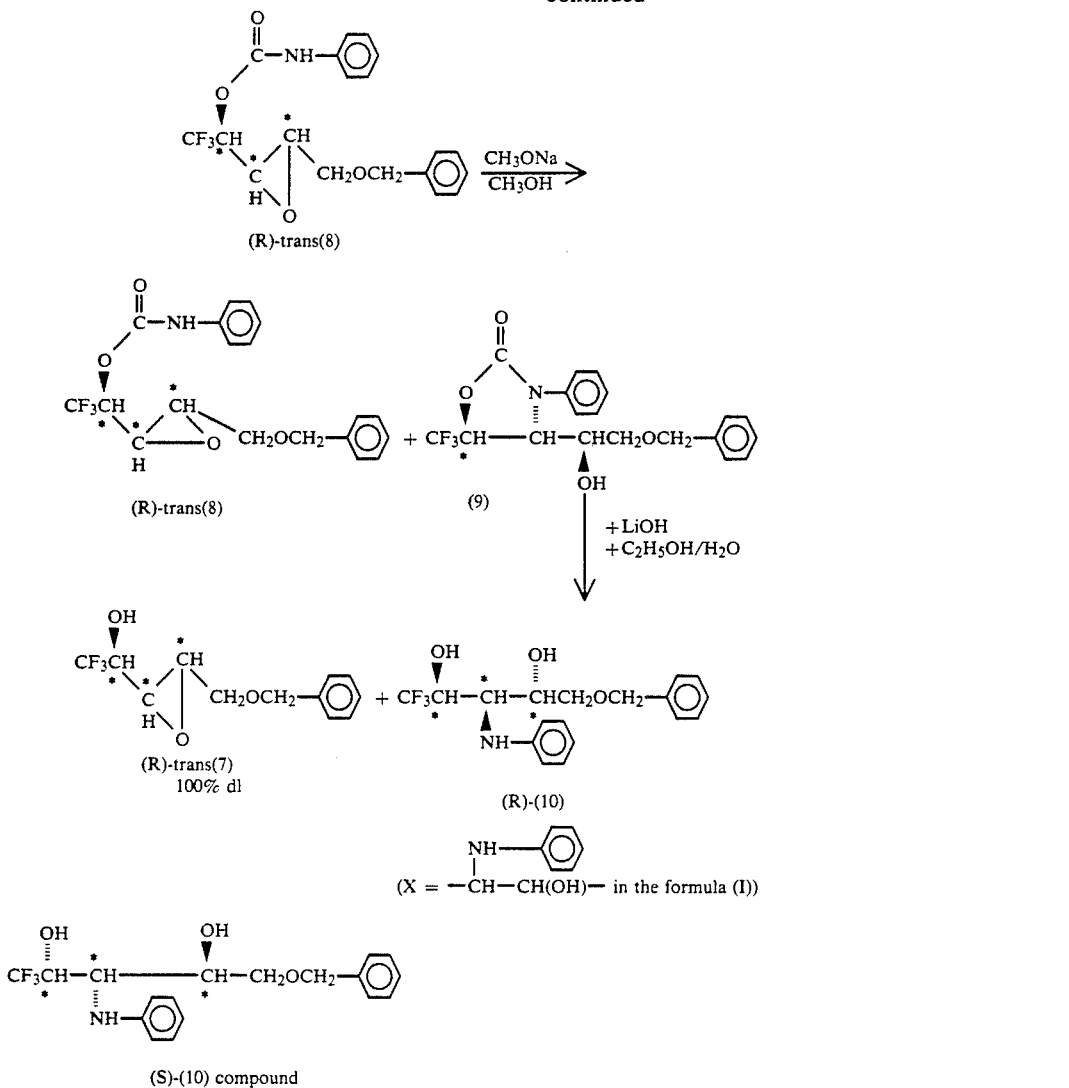
is prepared in the same procedure as above from (S)-(E)-(5) (trans)
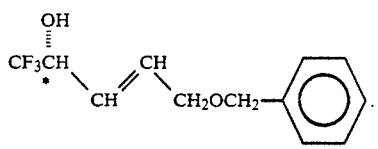
Reaction of the compound (Z)-(5) is also shown by the following chemical formulas.
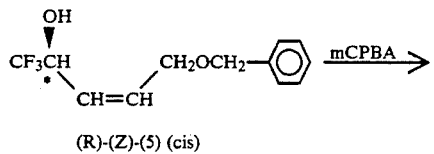
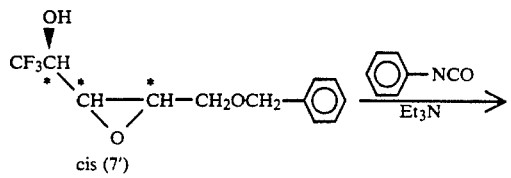

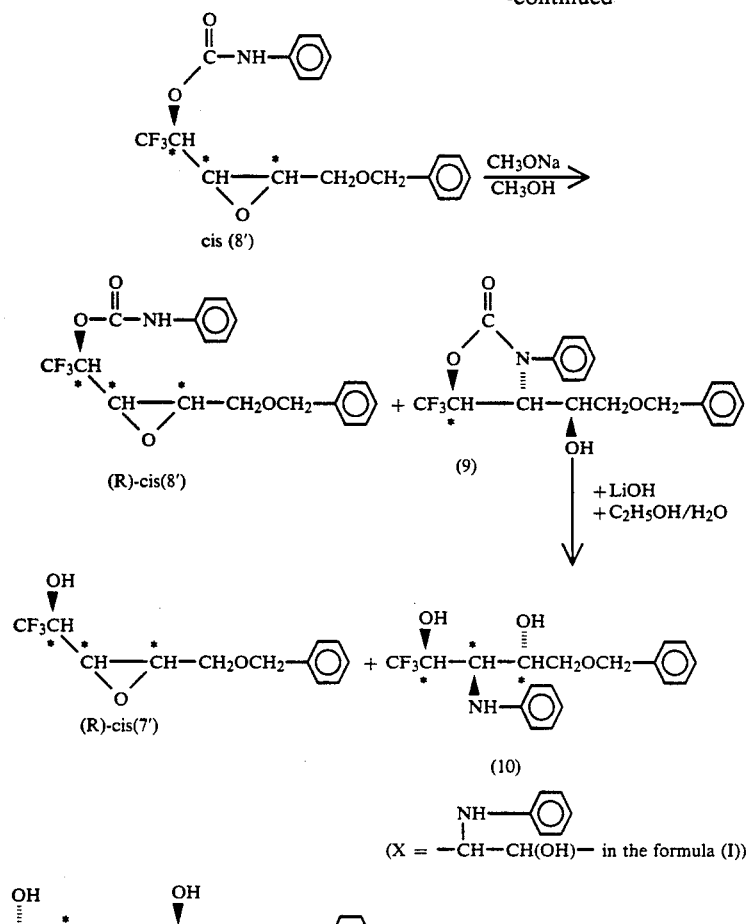

is prepared in the same manner as above from (S)-(Z)-(5) (cis)

Optically active compounds which are obtained by the present process are shown below.

| Configuration | Chemical structure |
|---|---|
| 2S, 3R, 4R | CF₃—CH(OH)—*CH—*CH—CH₂OCH₂OPh (epoxide) |
| 2S, 3S, 4S | CF₃—CH(OH)—*CH—*CH—CH₂OCH₂OPh (epoxide) |
| 2R, 3R, 4R | CF₃—CH(OH)—*CH—*CH—CH₂OCH₂OPh (epoxide) |
| 2R, 3S, 4S | CF₃—CH(OH)—*CH—*CH—CH₂OCH₂OPh (epoxide) |
| 2S, 3R, 4R | CF₃—CH(OH)—*CH—*CH—CH₂OCH₂Ph (epoxide) |
| 2S, 3S, 4S | CF₃—CH(OH)—*CH—*CH—CH₂OCH₂OPh (epoxide) |
| 2S, 3R, 4R | CF₃—CH(OH)—*CH—*CH—CH₂OCH₂Ph (epoxide) |
| 2R, 3S, 4S | CF₃—CH(OH)—*CH—*CH—CH₂OCH₂OPh (epoxide) |

| Configuration | Chemical structure |
|---|---|
| Anti-form | OH OH<br>CF₃—⋯—⋯—O—Ph<br>   NHPh |
| Anti-form | OH OH<br>CF₃—⋯—⋯—O—O—Ph<br>   NHPh |

The present invention will be explained in detail by the following examples.

EXAMPLES (1) Preparation of 1-benzyloxy-2-propyne (1)

4.6 g (192 mmol) of sodium hydride was charged in a 200 ml three-necked flask provided with a 100 ml dropping funnel with a bypass and vacuum-dried in nitrogen stream. Then, thereto was added 100 ml of tetrahydrofuran, followed by cooling to 0° C. Furthermore, 11.2 ml (192 mmol) of propargyl alcohol diluted with 100 ml of tetrahydrofuran was gradually added thereto. After stirring at this temperature for 30 minutes, 22.3 ml (160 mmol) of chloromethylbenzyl ether diluted with 20 ml of tetrahydrofuran was added dropwise, followed by stirring for 30 minutes. After further stirring for 1 hour at room temperature, the reaction was stopped by saturated aqueous ammonium chloride solution and the reaction mixture was rendered weakly acidic with 3N aqueous hydrochloric acid solution and extracted with methylene chloride. The organic layer was dried over anhydrous magnesium sulfate. The solvent was removed by vacuum distillation and then the ether (1) was obtained by vacuum distillation. Boiling point: 80–83° C./0.5 mmHg, Yield: 90%

¹H-NMRδ(ppm): 2.28(t.1H, J=3.0 Hz. CH≡C-); 4.28(d.2H, J=3.0 Hz CH≡C-CH₂); 4.63(s.2H, CH₂Ph); 4.83(s.2H, O-CH₂O); 7.58(s.5H, Ph).

IR(neat)(cm⁻¹): 3300(C≡C), 3050, 2900(CH₂), 1500(Ph)

(2) Preparation of 5-benzyloxy-1,1,1-trifluoro-3-pentyne-2-one (2)

4.2 g (172 mg-atm) of magnesium was charged in a 200 ml three-necked flask equipped with a Dimroth condenser and a 100 ml dropping funnel with a bypass and vacuum-dried in argon stream. Thereto were added 20 ml of dry tetrahydrofuran and 0.84 ml of ethyl bromide and after initiation of reaction, a solution prepared by dissolving 12.00 ml (total amount 12.84 ml, 172 mmol) of ethyl bromide in 140 ml of tetrahydrofuran was gradually added, followed by stirring for 1.5 hour to obtain Grignard reagent. Then thereto was added ether (1) (143 mmol) prepared by the method of the above (1) diluted with 20 ml of tetrahydrofuran over a period of 30 minutes, followed by stirring for 1 hour at 40° C. Then, separately, 28.4 g (200 mmol) of ethyl trifluoroacetate and 80 ml of tetrahydrofuran were charged in a 300 ml three-necked flask in argon stream and cooled to −98° C. Thereto was added the Grignard reagent obtained above over a period of 1 hour, followed by stirring at this temperature for 1.5 hour and then, for further 1 hour at 0° C.

Then, 1N aqueous hydrochloric acid solution was added thereto and the reaction mixture was made weakly acidic and extracted with methylene chloride. The organic layer was dried over magnesium sulfate and solvent was distilled off to obtain crude product ketone (2). This compound was susceptible to decomposition by distillation and so was used in the next step as it was without purification.

(3) Preparation of 5-benzyloxy-1,1,1-trifluoro-3-pentyne-2-ol (3)

1.85 g (48.9 mmol) of sodium borohydride and 100 ml of absolute ethanol were charged in a 200 ml eggplant type flask and then thereto was added a solution prepared by dissolving the crude ketone (the total amount) obtained in the above (2) in 60 ml of ethanol over a period of 1 hour under ice-cooling, followed by stirring at room temperature overnight. Ethanol was removed by vacuum distillation and thereafter, the reaction was stopped by adding saturated aqueous solution of ammonium chloride. Then, the reaction mixture was made weakly acidic with 1N aqueous hydrochloric acid solution and was extracted with methylene chloride. The organic layer was dried over anhydrous magnesium sulfate and then the solvent was distilled off to obtain a crude product. The resulting crude product was purified by silica gel column chromatography to obtain the above alcohol (3).

Yield: 88%

¹H-NMRδ(ppm): 3.63(bs.1H, OH); 4.30(d.2H, J=1.5 Hz CH|C-CH₂O-); 4 62[m.1H, CF₃CH(OH)]; 4.63(s.2H, CH₂Ph); 4.82(s.2H, O-CH₂O); 7.38(s.5H, Ph).

¹⁹F-NMR: 1.00(d, JH-F=5.6 Hz)

IR(neat)(cm⁻¹): 3400(OH), 3050, 2900(CH₂)

(4) Preparation of 2-acetoxy-5-benzyloxy-1,1,1-trifluoro-3-pentyne (4)

In a three-necked flask of 50 ml in internal volume which was well dried under reduced pressure in nitrogen stream were charged 20 ml of methylene chloride, 3.57 g (13.0 mmol) of the above alcohol (3) and 1.20 ml (16.9 mmol) of acetyl chloride and then 1.37 ml (16.9 mmol) of pyridine was added thereto under ice-cooling, followed by stirring at room temperature overnight. The reaction was stopped by adding 1N aqueous hydrochloric acid solution and the reaction mixture was extracted with methylene chloride and dried over anhydrous magnesium sulfate. Solvent was distilled off to obtain a crude product, which was purified by silica gel column chromatography to obtain the above acetate (4).

Yield: 96%

¹H-NMRδ(ppm): 2.17(s.3H, CH₃CO); 4.30(d.2H, J=1.5 Hz, CH|C-CH₂); 4.63(s.2H, CH₂Ph); 4.80(s.2H, O-CH₂O); 5.92 [tq.1H, J=1.5, 6.4 Hz, CF₃CH(OCOCH₃)]; 7.38(s.5H, Ph).

¹⁹F-NMR: −1.17(d, JH-F=6.4 Hz)

IR(neat)(cm⁻¹): 2950, 2900(CH₂), 1770(C=0)

For the corresponding isobutyrate, 5-benzyloxy-2-isobutyryloxy-1,1,1-trifluoro-3-pentyne was obtained in the same manner as for acetate.

¹H-NMRδ(ppm): 1.23 [d.6H, J=7.1 Hz.)(CH₃)₂CH.]; 2.67 [sep.1H, J=7.1 Hz)(CH₃)₂CH.]; 4.32(d.2H, J=2.0 Hz) CH|C-CH₂; 4.65(s.2H, CH₂Ph); 4.82(s.2H, O-CH₂O); 5.95(tq.1H, J=2.0, 6.0 Hz CF₃CH); 7.40(s.5H, Ph). ¹⁹F-NMR: −1.58(d, JH-F=6.0 Hz)

IR(neat)(cm⁻¹): 3000, 2950(CH₂), 1760(C=0)

(5) Asymmetric hydrolysis of acetate (4)

In an eggplant type flask of 200 ml in internal volume were charged 4.3 g (13.7 mmol) of the acetate obtained in the above (4), 2.3 g (135470 units) of lipase MY and 130 ml of distilled water, followed by stirring at 40°–41° C. Acetic acid produced in the system with progress of reaction was titrated with 1N aqueous sodium hydroxide solution to check degree of progress of hydrolysis. When suitable degree of hydrolysis was obtained, reaction mixture was filtrated by Celite. Then, filtrate was extracted with ethyl acetate and the organic layer was dried over anhydrous magnesium sulfate. Thereafter, solvent was distilled off under reduced pressure and the resulting crude product was purified by silica gel column chromatography where a moving phase was n-hexane/diethyl ether (10/1) to obtain 1.50 g (5.50 mmol) of the corresponding optically active alcohol (R)-(3) and 1.90 g (6.00 mmol) of optically active acetate (S)-(4) (recovery: 84%).

The same procedure as above was also carried out with using isobutyrate as a starting material. The results are shown in Table 1.

TABLE 1

| Starting Material (3) | Enzyme | Supplier | Degree of hydrolysis (%) | Optical purity (% ee) |
|---|---|---|---|---|
| Acetate | Lipase MY | Meito Sangyo Co. | 45 | 30 |
| Acetate | Lipase P "Amano" | Amano Seiyaku Co. | 33 | 49 |
| Isobutyrate | Lipase MY | Meito Sangyo Co. | 50 | — |
| Isobutyrate | Lipase P "Amano" | Amono Seiyaku Co. | 34 | 88 |

(6) Preparation of 5-benzyloxy-1,1,1-trifluoro-3-pentene-2-ol (E)-(5)

18 ml (61.2 mmol) of 3.4 N toluene solution of NaAlH$_2$(OCH$_2$CH$_2$OCH$_3$)$_2$(Red-Al ®) and 50 ml of dry diethyl ether were charged in a sufficiently dried 100 ml three-necked flask provided with a 50 ml dropping funnel with a bypass in nitrogen stream and cooled to −20° C. Thereto was added over a period of 30 minutes a solution prepared by diluting 14.0 g (51.0 mmol) of 5-benzyloxy-1,1,1-trifluoro-3-pentyne-2-ol (3) obtained in the above (3) with 50 ml of ether. Stirring was carried out at this temperature for 1 hour and then for further 1 hour at room temperature. The reaction was stopped by using 3 N aqueous hydrochloric acid solution and reaction mixture was extracted with ether, dried over anhydrous magnesium sulfate and concentrated. The resulting crude product was purified by silica gel column chromatography to obtain the compound (E)-(5). Yield 83%.

$^1$H-NMRδ(ppm): 2.85(d, 1H, J=6.0 Hz, OH); 4.15 (d, 2H, J=4.5 Hz, C=CH-CH$_2$); 4.38 (m, 1H, CF$_3$CH); 4.63 (s, 2H, CH$_2$Ph); 4.78 (s, 2H, O-CH$_2$O); 5.80 (dd, 1H, J=5.3, 16.5 Hz, CF$_3$CHCH=CH); 6.12 (dt, 1H, J=4.5, 16.5 Hz, CF$_3$CHCH=CH); 7.40 (s, 5H, Ph).

$^{19}$F-NMR: +0.75 (d, J$_{H-F}$=6.0 Hz)

IR(neat)(cm$^{-1}$): 3400 (OH), 3050, 2900 (CH$_2$) 980 (C=C trans)

(7) Preparation of 2-isobutoxy-5-benzyloxy-1,1,1-trifluoro-3-pentene (E)-(6)

To a solution of 11.6 g (42.0 mmol) of the compound (E)-(5) obtained in the above (6) and 5.3 ml (50.4 mmol) of isobutyric acid chloride in 50 ml of methylene chloride, was added 4.1 ml (50.4 mmol) of pyridine at 0° C. and temperature was returned to room temperature and the solution was stirred overnight. Then, reaction was terminated by 1N aqueous hydrochloric acid solution and the reaction mixture was extracted with methylene chloride and dried over anhydrous magnesium sulfate and solvent was distilled off under reduced pressure. The resulting crude product was purified by silica gel column chromatography to obtain the above isobutyrate (E)-(6). Yield: 84%.

$^1$H-NMRδ(ppm): 1.20 [d, 6H, J=7.1 Hz, CH(CH$_3$)$_2$]; 2.67 [sep.1H, J=7.1 Hz, CH(CH$_3$)$_2$]; 4.15(d, 2H, J=4.5 Hz, CH=CH-CH$_2$); 4.63(s, 2H, CH$_2$Ph; 4.80(s, 2H, O-CH$_2$-O-); 5.90(m, 2H, CF$_3$CH, CF$_3$CHCH=CH); 6.27(dt, 1H, J=4.2, 15.0 Hz, CF$_3$CHCH=CH; 7.40(s, 5H, Ph).

$^{19}$F-NMR: −1.17 (d, J$_{H-F}$=6.2 Hz)

IR(neat)(cm$^{-1}$): 3000, 2950(CH$_2$), 1760(C=0)

For the corresponding acetate, 2-acetoxy-5-benzyloxy-1,1,1-trifluoro-3-pentene (E)-(6) was also obtained in the same manner as for isobutyrate. Yield: 94%.

(8) Asymmetric hydrolysis of the above isobutyrate (E)-(6)

6.24 g (21.6 mmol) of the above isobutyrate (E)-(6), 7.2 g (216000 units) of lipase P (manufactured by Amano Seiyaku Co.), and 150 ml of distilled water were charged in an eggplant type flask of 50 ml in internal volume and stirred with keeping temperature at 40°–51° C. in a thermostatic bath. Isobutyric acid was produced in the reaction system with progress of reaction and degree of progress was checked with titrating the isobutyric acid with 1N aqueous sodium hydroxide solution. Reaction mixture was filtrated by Celite and extracted with ethyl acetate and dried over anhydrous magnesium sulfate and solvent was distilled off under reduced pressure. Crude product was purified by silica gel column chromatography where a moving phase was n-hexane/diethyl ether (10/1) to obtain 1.11 g (4.00 mmol, optical purity 98% ee) of the corresponding alcohol (R)-(E)-(5) and 5.06 g (14.6 mmol) of isobutyrate (R)-(E)-(6). Recovery: 86%.

When acetate (E)-(6) was used as a starting material, the above compound (R)-(E)-(5) was also similarly obtained. Recovery: 90%, optical purity 40% ee.

(9) Preparation of 5-benzyloxy-trans-3,4-epoxy-1,1,1-trifluoro-2-pentanol (7)

In an eggplant type flask of 100 ml in internal volume were charged at 0° C. 4.14 g (15.0 mmol) of 5-benzyloxy-1,1,1-trifluoro-3-pentene-2-ol (E)-(5), 5.29 g (30.7 mmol) of m-chloroperoxybenzoic acid (mCPBA) and 80 ml of methylene chloride, followed by stirring at room temperature overnight. Thereto was added saturated aqueous sodium sulfite solution to decompose excess mCPBA and then reaction mixture was extracted with methylene chloride. The organic layer was dried over anhydrous magnesium sulfate and then solvent was distilled off under reduced pressure. The resulting crude product was purified by silica gel column chromatography. The above trans epoxide (7) was obtained in a yield of 90%.

Diastereomer was a mixture of diastereomers of 55:45 from integral ratio of a peak appearing in low magnetic field and a peak appearing in high magnetic field in $^{19}$F-NMR.

$^{19}$F-NMR: −0.47(d, J$_{H-F}$=7.5 Hz); −0.42(d, J$_{H-F}$=7.2 Hz)

(10) Preparation of 5-benzyloxy-trans-3,4-epoxy-2-[(N-phenylcarbamoyl)oxy]-1,1,1-trifluoropentane (8)

In a 50 ml three-necked flask dried under reduced pressure were charged 2.94 g (10.1 mmol) of the epoxide [trans-(7)] obtained in the above (9), 1.30 ml (1.20 mmol) of phenyl isocyanate (PhNCO), and 30 ml of methylene chloride and was further added 1.81 ml (13.0 mmol) of triethylamine. The temperature was maintained to room temperature and stirring was conducted overnight. Thereafter, reaction was stopped by 1N aqueous hydrochloric acid solution and reaction mixture was extracted with methylene chloride. The methylene chloride layer was dried over anhydrous magnesium sulfate and solvent was distilled off under reduced pressure. The resulting composition was purified by silica gel column chromatography to obtain the above carbamate. Yield 89%.

$^{19}$F-NMR: −3.5(d, $J_{H-F}$=6.6 Hz); −3.1(d, $J_{H-F}$=6.4 Hz)

(11) Preparation of 5-benzyloxy-3-(N-phenylamino)-1,1,1-trifluoropentane-2,4-diol (10)

(a) Preparation of epoxide trans-(7) and urethane (9)

In 100 ml eggplant type flask were charged 3.42 g (9.0 mmol) of the carbamate trans (8) prepared in the above (10), 1.08 g (20 mmol) of methoxysodium and 50 ml of methanol, followed by stirring overnight. Reaction was stopped by adding water and reaction mixture was extracted with methylene chloride. The organic layer was dried over anhydrous magnesium sulfate and solvent was distilled off under reduced pressure. The resulting crude product was purified by silica gel column chromatography to obtain epoxide trans-(7) and urethane (9) as a mixture.

The two products were respectively pure compounds as diastereomers. NMR spectra of the resulting compounds are as follows.

$^{19}$F-NMR: −0.25(d, $J_{H-f}$=6.6 Hz); +1.58(d, $J_{H-F}$=6.6 Hz)

(b) Preparation of aminodiol (10)

The mixture obtained in the above (a) was dissolved in a mixture of 30 ml of ethanol and 10 ml of water and the solution was charged in a 50 ml eggplant type flask. Thereto was added 0.06 g (30.0 mmol) of lithium hydroxide, followed by stirring overnight. Then, water was added to stop the reaction and the reaction mixture was extracted with methylene chloride. The organic layer was dried over anhydrous magnesium sulfate and concentrated. The resulting crude product was purified by silica gel column chromatography to isolate aminodiol (10) and epoxide trans-(7). Two-stage total yield: 60%. NMR spectrum of the aminodiol (10) was as follows.

$^1$H-NMRδ(ppm): 3.28(bs, 1H, NHPh); 3.83 [bs, 2H, CH(OH)CH$_2$O]; 3.80~4.20 [m, 4H, OH, OH, CHNHPh, CH(OH)CH$_2$O[; 4.60(s, 2H, CH$_2$Ph); 4.43-4.95(m, 3H, CF$_3$CH, OCH$_2$O); 6.63~7.5(m, 5H, NHPh); 7.42(s, 5H, CH$_2$Ph).

$^{19}$F-NMR: −2.30(d, $J_{H-F}$=7.5 Hz)

What is claimed is:

1. 1,1,1-trifluror-2-hydroxy-5-benzyloxy compound represented by the following formula (I) and optical isomers thereof:

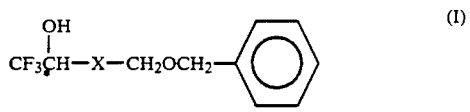
(I)

wherein X represents a

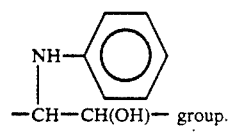
group.

2. Optical isomers of the compound shown by the following formula:

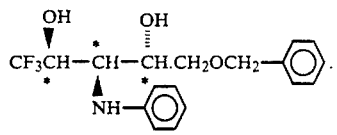

* * * * *